United States Patent
Segal et al.

(10) Patent No.: US 11,590,100 B2
(45) Date of Patent: *Feb. 28, 2023

(54) COMPOSITION FOR BUCCAL OR SUBLINGUAL ADMINISTRATION OF CANNABIS EXTRACT AND METHODS FOR MAKING SAME

(71) Applicant: PANAXIA PHARMACEUTICAL INDUSTRIES LTD., Lod (IL)

(72) Inventors: David Segal, Tel Aviv (IL); Eran Goldberg, Ramat Gan (IL); Shany Hershkovits, Mazor (IL); Hagai Moshe, Givat Shmuel (IL)

(73) Assignee: PANAXIA PHARMACEUTICAL INDUSTRIES LTD., Lod (IL)

( * ) Notice: Subject to any disclaimer, the term of this patent is extended or adjusted under 35 U.S.C. 154(b) by 36 days.

This patent is subject to a terminal disclaimer.

(21) Appl. No.: 17/234,948

(22) Filed: Apr. 20, 2021

(65) Prior Publication Data

US 2021/0236459 A1  Aug. 5, 2021

Related U.S. Application Data (63) Continuation of application No. 16/481,975, filed as application No. PCT/IL2018/050113 on Feb. 1, 2018, now Pat. No. 11,007,170.

(60) Provisional application No. 62/453,619, filed on Feb. 2, 2017.

(51) Int. Cl.
*A61K 31/352* (2006.01)
*A61K 9/00* (2006.01)
*A61K 9/16* (2006.01)
*A61K 9/20* (2006.01)

(52) U.S. Cl.
CPC ............ *A61K 31/352* (2013.01); *A61K 9/006* (2013.01); *A61K 9/1611* (2013.01); *A61K 9/2009* (2013.01)

(58) Field of Classification Search
None
See application file for complete search history.

(56) References Cited

U.S. PATENT DOCUMENTS

| 4,338,098 | A | 7/1982 | Teijo |
| 6,465,709 | B1 | 10/2002 | Sun et al. |
| 6,890,553 | B1 | 5/2005 | Sun et al. |
| 11,007,170 | B2 * | 5/2021 | Segal .................. A61K 9/0053 |
| 2004/0229939 | A1 | 11/2004 | Chowdhury et al. |

(Continued)

FOREIGN PATENT DOCUMENTS

| CN | 104473171 A | 4/2015 |
| CN | 106212978 A | 12/2016 |

(Continued)

OTHER PUBLICATIONS

N. Krispil, "Medicial Plants: a field guide to the medicinal plants of the Land of Israel" (in Hebrew). Har Gilo, Israel 1986.

(Continued)

*Primary Examiner* — Melissa S Mercier
(74) *Attorney, Agent, or Firm* — The Roy Gross Law Firm, LLC; Roy Gross (57) ABSTRACT

A thermogenic cannabis composition for oral administration, including cannabis extract and at least one thermogenic agent, and method of producing same.

19 Claims, 1 Drawing Sheet

(56) References Cited

U.S. PATENT DOCUMENTS

| | | |
|---|---|---|
| 2007/0141184 A1 | 6/2007 | Verneau |
| 2010/0008985 A1* | 1/2010 | Pellikaan ................ A61P 21/00 424/464 |
| 2014/0166027 A1 | 6/2014 | Fuisz et al. |
| 2014/0302086 A1 | 10/2014 | Kelly |
| 2014/0302142 A1 | 10/2014 | Klimova |
| 2015/0037394 A1 | 2/2015 | Wood et al. |
| 2015/0374770 A1 | 12/2015 | Crowley |
| 2016/0030473 A1 | 2/2016 | Dennett, Jr. et al. |
| 2016/0199299 A1 | 7/2016 | Uren |
| 2016/0296464 A1 | 10/2016 | Lindsay |

FOREIGN PATENT DOCUMENTS

| | | |
|---|---|---|
| CN | 107126414 A | 9/2017 |
| JP | 2013079219 B2 | 5/2013 |
| WO | 2016100516 A1 | 6/2016 |
| WO | 2016193983 A1 | 12/2016 |
| WO | 2017059859 A1 | 4/2017 |
| WO | 2017093714 A1 | 6/2017 |

OTHER PUBLICATIONS

R. Cech "Making plant medicine." Horizon Herbs, 2000.
Extended European Search Report, European Application No. 18747438, dated Dec. 10, 2019.
PCT Search Report for International Application No. PCT/IL2018/050113; dated Mar. 27, 2018; 4 pp.
PCT Written Opinion for International Application No. PCT/IL2018/050113; dated Mar. 27, 2018; 6 pp.
PCT Preliminary Report for International Application No. PCT/IL2018/050113; dated Aug. 6, 2019 ; 7 pp.
Pub Chem, Citric Acid product information sheet, accessed Oct. 29, 2020). (Year: 2020).

* cited by examiner

COMPOSITION FOR BUCCAL OR SUBLINGUAL ADMINISTRATION OF CANNABIS EXTRACT AND METHODS FOR MAKING SAME

RELATED APPLICATIONS

This application is a Continuation of U.S. patent application Ser. No. 16/481,975 filed on Jul. 30, 2019, which is a National Phase of PCT Patent Application No. PCT/IL2018/050113 having International filing date of Feb. 1, 2018, which claims the benefit of priority of U.S. Provisional Application No. 62/453,619 filed on Feb. 2, 2017. The contents of the above applications are all incorporated by reference as if fully set forth herein in their entirety.

FIELD OF THE INVENTION

The present disclosure generally relates to the field of cannabis compositions for oral administration comprising a thermogenic agent, enhancing buccal and/or sublingual absorption properties.

BACKGROUND

Historically, the plant world has been the most important source of medicinal agents for the treatment of human and animal disease, and for use as preventative agents in maintaining good health. However, for at least the last 150 years, Western medicine has been dominated by synthetic chemical agents.

It is now being increasingly recognized, however, that many plants and plant extracts are highly effective agents for the prevention and treatment of disease. A single plant can possess a large number of pharmaceutically active agents, and extracts obtained therefrom can exert their activities on a variety of physiologic processes, increasing the range of the desired therapeutic effect.

One such plant which medicinal use has been recognized is the cannabis plant. Delta-9-tetrahydrocannabinol (THC, also referred to as Dronabinol), an extract of the cannabis plant, exhibits complex effects on the central nervous system (CNS), including central sympathomimetic activity. THC demonstrates effects on appetite, mood, cognition, memory and perception. Furthermore, the drug has anti-emetic properties and is used to control nausea and vomiting associated with cancer chemotherapy and has also been found as an effective means to treat pain.

Another cannabinoid with well-documented health benefits is cannabidiol (CBD). In contrast to THC, CBD does not exert psychoactive effects. CBD is reported to have antidepressant, anti-anxiety, anti-inflammatory, and neuroprotective effects.

Despite the numerous benefits associated with THC and CBD, when administered in oral form, the onset of action can be slow, which can detract from their usefulness in some instances. For example, after oral administration, THC has an onset of action of fifteen minutes at the very earliest to 1.5 hours and a peak effect at 2-4 hours. THC is almost completely absorbed (90-95%) after single oral doses. However, due to a combined effect of first pass hepatic metabolism and poor aqueous solubility (THC water solubility is 2.8 mg/L), only 10-20% of the administered dose reaches the systemic circulation. Therefore, oral consumption of cannabis is characterized by low bioavailability of cannabinoids, and slow onset of action. Thus, as this one example provides, there is a need for improved cannabinoid based compositions for oral administration.

SUMMARY

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other advantages or improvements.

According to some embodiments, there is provided a thermogenic composition for oral administration comprising at least one cannabinoid and at least one thermogenic agent.

The present inventors surprisingly found that the addition of a thermogenic agent to the cannabis extract tablet composition significantly increased the rate and efficiency of buccal and/or sublingual absorption, thus increasing the bioavailability of the cannabinoids. Advantageously, the herein disclosed tablets further ease dosage adjustments and thus allow for accurate and reproducible therapeutic effects.

According to some embodiments, there is provided a thermogenic cannabis composition for oral administration, the composition comprising at least one cannabinoid and at least one thermogenic agent.

According to some embodiments, the thermogenic agent comprises calcium chloride (CaCl2), calcium sulfate (MgSO4), calcium nitrate (Ca(NO3)2), calcium carbonate (CaCO3), calcium oxide (CaOH), calcium bromide (CaBr2), calcium iodide (CaI2), potassium phosphate (K3PO4), magnesium chloride (MgCl2), magnesium sulfate (MgSO4) magnesium nitrate (Mg(NO3)2), magnesium carbonate (MgCO3), magnesium bromide (MgBr2), magnesium iodide (MgI2), sodium carbonate (Na2NO3) potassium carbonate (K2NO3), sodium acetate (NaC2H3O2), potassium acetate (KC2H3O2), sodium oxide (NaOH), potassium oxide (KOH), citric acid ($C_6H_8O_7$), lithium chloride (LiCl), lithium bromide (LiBr), lithium iodide (LiI), lithium sulfate (Li2SO4) or any combination thereof. According to some embodiments, the thermogenic agent comprises calcium chloride ($CaCl_2$)), magnesium sulfate ($MgSO_4$), magnesium chloride ($MgCl_2$) or any combination thereof. According to some embodiments, the thermogenic agent is anhydrous.

According to some embodiments, the thermogenic composition is capable of reaching temperatures of at least 40° C., and no more than 80° C., when exposed to a 37° C. aqueous environment in a 1:1 ratio. According to some embodiments, the thermogenic composition is adapted to reach a temperature of between 40° C. and 60° C. inclusive, when exposed to a 37° C. aqueous environment in a 1:1 ratio. According to some embodiments, the thermogenic composition is adapted to reach a temperature of between 42° C. and 50° C. inclusive, when exposed to a 37° C. aqueous environment in a 1:1 ratio. According to some embodiments, the thermogenic composition is adapted to remain above 37° C. for at least until the composition is fully dissolved in a 1:1 ratio in a 37° C. aqueous environment.

According to some embodiments, the thermogenic cannabis composition comprises 1% to 90% w/w of the at least one cannabinoid. According to some embodiments, the thermogenic cannabis composition comprises 0.1 mg to 100 mg of the at least one cannabinoid per dosage unit. According to some embodiments, the thermogenic cannabis composition comprises about 2-25 mg of the at least one cannabinoid per dosage unit.

According to some embodiments, the thermogenic cannabis composition comprises 0.1 mg to 100 mg THC per dosage unit. According to some embodiments, the thermogenic cannabis composition comprises about 2-25 mg THC per dosage unit.

According to some embodiments, the thermogenic cannabis composition comprises 0.1 mg to 100 mg CBD per dosage unit. According to some embodiments, the thermogenic cannabis composition comprises about 2-25 mg CBD per dosage unit.

According to some embodiments, the thermogenic cannabis composition comprises 5%-60% w/w thermogenic agent. According to some embodiments, the thermogenic cannabis composition comprises 10%-30% w/w thermogenic agent.

According to some embodiments, the thermogenic cannabis composition comprises a sweetener and/or a flavoring substance. According to some embodiments, the sweetener is sucralose. According to some embodiments, the flavoring substance is selected from the list consisting of: menthol, vanilla, mango, lemon, strawberry, blueberry, chocolate, blackcurrant, watermelon, pear, anise, pineapple, apple, orange, banana, grapefruit, butter, honey, cherry, melon, mocha, mandarin, apricot, peppermint, grape, caramel, raspberry, cinnamon, kiwi, coffee, cocoa, tea, rum and cola.

According to some embodiments, the oral administration is buccal and/or sublingual administration and wherein said thermogenic agent enhances buccal and/or sublingual absorption of the cannabis extract. According to some embodiments, the thermogenic composition is a tablet, a granulate, or a powder.

According to some embodiments, there is provided a method of increasing the efficiency of buccal and/or sublingual absorption of cannabinoids by administering to a subject in need thereof the composition as essentially disclosed herein, thereby increasing the efficiency of buccal and/or sublingual absorption.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

The invention will now be described in relation to certain examples and embodiments with reference to the following illustrative figures so that it may be more fully understood.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Definitions

Cannabinoids

The term "cannabinoid" refers hereinafter to a class of diverse chemical compounds that act on cannabinoid receptors present in cells that repress neurotransmitter release in the brain. Cannabinoid compounds may include the endocannabinoids (produced naturally in the body by humans and animals), the phytocannabinoids (found in cannabis and some other plants), and synthetic cannabinoids. According to some embodiments, the at least one cannabinoid of the composition may be in the form of an extract including the cannabinoid, a purified or distilled cannabinoid or combination of cannabinoids derived from an extract, or a cannabinoid or combination of cannabinoids synthetically produced.

The term "cannabidiol (CBD)" refers hereinafter to one of at least 85 known active cannabinoids. Cannabidiol is a major phytocannabinoid. CBD is considered to have a wider scope of medical applications than Tetrahydrocannabinol (THC). Cannabidiol has a very low affinity for CB1 and CB2 receptors, but acts as an indirect antagonist of their agonists. Without being bound by any theory, CBD may potentiate THC's effects by increasing CB1 receptor density or through another CB1-related mechanism. CBD is also an inverse agonist of CB2 receptors. CBD possesses antiproliferative, pro-apoptotic effects and inhibits cancer cell migration, adhesion and invasion.

According to some embodiments, the cannabidiol (CBD) or a derivative thereof may be selected from the group consisting of CBD, CBDV, CBDA, CBDN and any combination thereof. Each possibility is a separate embodiment.

According to some embodiments, the cannabidiol (CBD) or a derivative thereof may be selected from the group consisting of natural CBD or a derivative thereof produced in the body of humans and animals, CBD or a derivative thereof extracted from plants, synthetic CBD or a derivative thereof, and any combination thereof. Each possibility is a separate embodiment. According to some embodiments, the cannabidiol (CBD) or a derivative thereof is CBD extracted from plants. According to some embodiments, the composition may include about 0.1 mg to about 100 mg THC per dosage unit (e.g. per tablet).

The term "Tetrahydrocannabinol (THC)" refers hereinafter to the principal psychoactive constituent (or cannabinoid) of the cannabis plant. THC has a partial agonist activity on the cannabinoid receptor CB1, and the CB2 receptor. THC may refer to delta-9-tetrahydrocannabinol, delta-6-tetrahydrocannabinol, delta-8-tetrahydrocannabinol and delta-1-tetrahydrocannabinol. Each possibility is a separate embodiment.

According to some embodiments, THC or a derivative thereof is selected from the group consisting of THC, THCV, THCA, THCVA and any combination thereof. Each possibility is a separate embodiment.

According to some embodiments, the composition may include about 0.5 mg to about 100 mg cannabinoid per dosage unit (e.g. per tablet). According to some embodiments, the composition may include about 2 mg to about 50 mg cannabinoid per dosage unit. In other embodiments, the composition is formulated for administration of about 5 mg to about 10 mg cannabinoid per dosage unit. In yet other embodiments, the composition may include about 0.1 mg to about 100 mg cannabinoid per dosage unit.

Non-limiting examples of suitable cannabinoids include Tetrahydrocannabinol (THC), Tetrahydrocannabinolic acid (THCA), Cannabidiol (CBD), Cannabidiolic Acid (CBDA), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Cannabielsoin (CBE), Cannabicitran (CBT) or any combination thereof. Each possibility is a separate embodiment.

According to some embodiments, the composition may include about 2 mg to about 15 mg THC per dosage unit (e.g. per tablet). According to some embodiments, the composition may include about 5 mg to about 10 mg THC per dosage unit (e.g. per tablet). In other embodiments, the composition is formulated for administration of about 5 mg to about 10 mg THC per dosage unit. In yet other embodiments, the composition may include about 0.1 mg to about 100 mg THC per dosage unit.

The embodiments of the present invention contemplate dosage forms (e.g. tablets) with a total weight of between approximately 1 mg and 5 grams, or between approximately 0.25 grams and 0.5 grams, depending on the formulation of the API, size of the lozenge or tablet. According to some embodiments, the total weight of the tablet may be about 300 mg. This dosage form can be used for all natural, semi-synthetic and synthetic derivatives of all cannabinoids. Handling and processing of the extract is significant for proper delivery of the thereof, with the associated terpenes and flavonoids, all of which synergistically work to improve the medicinal value of the cannabinoids chosen for the particular ailment under treatment.

According to some embodiments, the composition further may include both THC and CBD or derivatives thereof. According to some embodiments, the composition may provide a synergistic effect with respect to relieving a medical condition as compared to the effect provided by THC or a derivative thereof or by CBD or a derivative thereof administered separately.

According to some embodiments, the cannabinoid (e.g. THC anchor CBD) or derivatives thereof may be extracted from a cannabis plant selected from a group consisting of: *Cannabis saliva*, *Cannabis indica*, *Cannabis ruderalis*, and any combination thereof. Each possibility is a separate embodiment.

As used herein, the term "cannabis extract" refers to any extract that can be obtained by any suitable technique for extracting cannabis resin from a cannabis plant.

The extracts may be produced by cold extraction techniques using a variety of different extraction solvents including water, fatty solvents (such as olive oil), and alcoholic solvents (e.g. 70% ethanol). Cold extraction techniques are typically applied to softer parts of the plant, such as leaves and flowers, or in cases wherein the desired active components of the plant are heat labile. Alternatively, the aforementioned solvents may be used to produce extracts of the desired plants by a hot extraction technique, wherein said solvents are heated to a high temperature, the precise value of said temperature being dependent on the properties of the chosen solvent and maintained at that temperature throughout the extraction process. Hot extraction techniques are more commonly applied to the harder, tougher parts of the plant, such as bark, woody branches and larger roots. In some cases, sequential extractions can be performed in more than one solvent, and at different temperatures. The plant extract may be used in a concentrated form. Alternatively, the extract may be diluted as appropriate to its intended use.

Procedures for producing plant extracts (including hot extraction, cold extraction and other techniques) are described in publications including "Medicinal plants: a field guide to the medicinal plants of the Land of Israel (in Hebrew), author: N. Krispil, Har Gilo, Israel, 1986" and "Making plant medicine, author: R. Cech, pub. by Horizon Herbs, 2000".

As a non-limiting example, the extract can be obtained by simply shaking or scraping resin off a Cannabis plant.

As another non-limiting example, butane or carbon dioxide can be used as a solvent for extraction.

As another non-limiting example, the Cannabis plant may be dried and ground into fine material. The ground material may then be mixed with a food-grade alcohol (such as at a ratio of of ground material to 1.5 gallons of alcohol), so that the ground material becomes fully immersed in the alcohol. The mixture may then be placed in a covered container and heated for 3 hours at 190° F., while refluxing the alcohol so as to distill the oils from the ground material. After allowing the mixture to cool, it may be passed through a strainer to separate liquid from solid plant residue. The liquid may then be separated such as by pouring through a filter. The filtered liquid contains alcohol and Cannabis extract. In order to remove the alcohol, the filtered liquid may be subjected to an evaporative process, such as heating, leaving the Cannabis extract behind.

As another non-limiting example, the Cannabis plant may be dried and ground into fine material, and then immersed in alcohol. The mixture may then be filtered, separating the liquid from the plant material. The alcoholic liquid containing diluted cannabinoids may then be partially evaporated to reach a high concentration of cannabinoids. The concentrated alcoholic extract may subsequently be winterized to remove waxes by incubation in sub-zero temperature, sedimentation of the waxes and cold filtration of the mixture. The remaining alcohol may then be evaporated to obtain an extract in the form of a resin. The extract may then be decarboxylated by placing in an oven at ≥100° C. for at least 1 hour. An extract with 40-90% cannabinoid content is thereby typically obtained.

Composition for Oral Administration

According to some embodiments, the composition for oral administration may be a syrup, drops, solution, suspension, tablet, bolus, troche, capsule and any combination thereof. Each possibility is a separate embodiment.

According to some embodiments, the composition may further include inactive ingredients selected from a group consisting of antiadherents, binders, coatings, disintegrants, flavours, colours, lubricants, glidants, sorbents, preservatives, sweeteners, and any combination thereof. Each possibility is a separate embodiment.

Non-limiting examples of suitable flavoring agents include sugar, sucrose, sorbitol, sucralose, saccharin sodium, sodium cyclamate, aspartame, neotame, acesulfame potassium, stevioside, sodium chloride, D-limonene, menthol, citric acid and any combination thereof. Each possibility is a separate embodiment.

Non-limiting examples of suitable preservatives include methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzoate, potassium benzoate, calcium benzoate, sodium metabisulfite, propylene glycol, benzaldehyde, butylated hydroxytoluene, butylated hydroxyanisole, formaldehyde donors, essential oils, monoglyceride, phenol, mercury components and any combination thereof. Each possibility is a separate embodiment.

Thermogenic Agents

A "thermogenic agent", as used herein, refers to any agent that is suitable for oral administration and which reacts with water or other aqueous liquids in an exothermic reaction. According to some embodiments, the thermogenic agent may refer to any agent having a negative enthalpy of solution. According to some embodiments, the thermogenic agent may refer to any agent having an enthalpy of solution below −10 KJ/mol.

The herein disclosed thermogenic composition may include any thermogenic agent. Preferably, the parameters associated with heat generation are controllable by the patient or caregiver.

According to some embodiments, the thermogenic agent may be a salt, which yields heat when hydrated. According to some embodiments, the composition may be or include a supercooled salt solution, which may be activated to yield heat, for example, by adding a crystal. Supercooled or metastable salt solutions can produce heat as a result of a trigger condition. A supercooled solution is produced by heating a salt above its melting point, e.g. sodium acetate or sodium thiosulphate, until it is fully melted, usually in the presence of a solvent, such as water. The mixture is then allowed to cool, and the salt effectively becomes supersaturated in the vehicle whilst remaining in solution. Exothermic crystallisation of the salt can be initiated by a trigger condition, such as a shear, or by the introduction of a nucleating agent (e.g. seed crystals). Such salts are disclosed in U.S. patent application Ser. No. 14/128,457.

Non-limiting examples of suitable salts include: calcium chloride ($CaCl_2$)), calcium sulfate ($CaSO_4$), calcium nitrate ($Ca(NO_3)_2$), calcium carbonate ($CaCO_3$), calcium oxide (CaOH), calcium bromide ($CaBr_2$), calcium iodide ($CaI_2$), potassium phosphate ($K_3PO_4$), magnesium chloride ($MgCl_2$), magnesium sulfate ($MgSO_4$) magnesium nitrate ($Mg(NO_3)_2$), magnesium carbonate ($MgCO_3$), magnesium bromide ($MgBr_2$), magnesium iodide ($MgI_2$), sodium carbonate ($Na_2NO_3$) potassium carbonate ($K_2NO_3$), sodium acetate ($NaC_2H_3O_2$), potassium acetate ($KC_2H_3O_2$), sodium oxide (NaOH), potassium oxide (KOH), citric acid ($C_6H_8O_7$), lithium chloride (LiCl), lithium bromide (LiBr), lithium iodide (LiI), lithium sulfate ($Li_2SO_4$) or any combination thereof. Each possibility is a separate embodiment. According to some embodiments, the salt may be calcium chloride ($CaCl_2$)), magnesium chloride ($MgCl_2$), magnesium sulfate ($MgSO_4$) or any combination thereof. Each possibility is a separate embodiment. According to some embodiments, the salts may be the anhydrous forms of the salts such as anhydrous calcium chloride ($CaCl_2$)), anhydrous magnesium chloride ($MgCl_2$) or anhydrous magnesium sulfate ($MgSO_4$). Other suitable salts include metal salts, oxides (e.g. calcium oxide and magnesium oxide) and/or hydroxides.

As used herein, the term "anhydrous" may refer to a salt having no water content or residual water content only, e.g. less than 5%, less than 1%, less than 0.1% or less than 0.01% w/w water. Each possibility is a separate embodiment. According to some embodiments, the composition may include a water content in the range of 5-30%.

According to some embodiments, the composition comprises 2%-70%, 5%-60%, 10%-50%, 10%-40% or 10%-30% w/w of the thermogenic agent.

According to some embodiments, the thermogenic agent may include monomers capable of yielding heat as a result of polymerization, triggered, for example, by adding a suitable catalyst.

According to some embodiments, the exothermic reaction may be caused by oxidation of iron.

According to some embodiments, the exothermic reaction may be caused by water or other aqueous solution to propylene glycol or glycerine.

According to some embodiments, the thermogenic composition is capable of reaching temperatures of at least 40 degrees centigrade, and preferably no more than 80 degrees Celsius, when exposed to an aqueous solution in a 1:1 ratio as essentially described herein. Depending on the system used to generate the heat, the skilled person is capable of selecting the quantity of heat generating ingredients and the volume of solvent in order to achieve at least 40 degrees centigrade and keep the maximum temperature below 80 degrees Celsius. A preferred temperature range is between 42 degrees Celsius and 60 degrees Celsius inclusive, or between 40-55 degrees Celsius.

According to some embodiments, the temperature of the composition may be measured by placing a beaker slightly submerged in a water bath having a temperature of 37° C. The composition is added to the beaker as well as water (or other aqueous solution, order irrelevant) in a ratio of 1:1 (w/w) and stirred until the composition is dissolved. The temperature increase ($\Delta T$) caused by dissolution of the composition, as compared to baseline (just before addition of composition/water), is measured.

In some embodiments, the thermogenic composition generates heat by hydration, and is achieved by mixing water, or other suitable solvent, with the salt, or other thermogenic agent to be hydrated, either in situ (e.g. as a result of sublingual administration), or immediately before use by adding the water to the composition immediately before administration to the patient.

As used herein, the term "about" refers to a range of values+10% of a specified value. For example, the phrase "about 10" includes ±10% of 10, or from 9 to 11.

EMBODIMENTS OF THE INVENTION

In one embodiment, there is provided a composition for oral administration and methods for making a composition comprising: cannabis extracts and at least one thermogenic agent.

According to some embodiments, adding the thermogenic agent to the composition provided any of the following benefits: increased absorption, increased bioavailability, faster onset of action, higher peak concentrations, faster time to peak concentrations, shorter duration of action (each of these improvements may be verified by pharmacokinetic studies). Additional benefits include: increased subjective therapeutic efficacy, and increased objective therapeutic efficacy which can be assessed by clinical evaluation. Each possibility is a separate embodiment. According to some embodiments, the onset of action of the herein disclosed composition is at least 5%, at least 10%, at least 20%, at least 50%, at least twice, at least three times or at least four times as fast as the same composition devoid of thermogenic agent.

In some embodiments, the composition for oral administration is in the form of a syrup, drops, a solution, a suspension, a powder, a granulate, a tablet, a bolus, a troche, a capsule and any combination thereof.

In some embodiments, the tablet comprises between 0.1 mg to 100 mg cannabinoids, between 1 mg to 90 mg cannabinoids, between 1 mg to 80 mg cannabinoids, between 1 mg to 70 mg cannabinoids, between 1 mg to 60 mg cannabinoids, between 1 mg to 50 mg cannabinoids, between 1 mg to 40 mg cannabinoids, between 1 mg to 30 mg cannabinoids, between 1 mg to 20 mg cannabinoids, between 1 mg to 10 mg cannabinoids, between 1 mg to 200 mg cannabinoids, between 1 mg to 300 mg cannabinoids, or between 2 mg to 7 mg cannabinoids. Each possibility is a separate embodiment. According to some embodiments, the tablet comprises up to 100 mg cannabinoids.

According to some embodiments, the tablet comprises about 0.5 mg to about 50 mg, or about 1 mg to about 20 mg THC, or about 2 mg to about 10 mg THC. Each possibility is a separate embodiment. According to some embodiments, the tablet comprises about 5 mg THC. According to some embodiments, the composition comprises between about 1% w/w to about 10% w/w of THC or a derivative thereof.

According to some embodiments, the tablet comprises about 0.5 mg to about 50 mg, or about 1 mg to about 20 mg CBD, or about 2 mg to about 10 mg CBD. Each possibility is a separate embodiment. According to some embodiments, the tablet comprises about 5 mg CBD. According to some embodiments, the composition comprises between about 1% w/w to about 10% w/w of CBD or a derivative thereof.

According to some embodiments, the composition comprises at least 80% by weight, and preferably at least 90% by weight, of THC and CBD, as calculated from the total weight of the cannabinoids present in the composition. According to some embodiments, the THC:CBD ratio by weight of the composition is wherein said predefined ratio of said CBD and said THC is selected from the group consisting of: about 0.1:100, 1:1, 5:1, 1:5, 1:4 4:1, 3:1, 1:3, 1:2, 2:1, 100:0.1. According to some embodiments, the composition comprises purified THC. According to some embodiments, the composition comprises purified CBD. According to some embodiments, the composition comprises distilled THC. According to some embodiments, the composition comprises distilled CBD. In this connection, the stated values for the total weight correspond to the cannabinoids present in the composition. The values for the THC:CBD ratios by weight may be values calculated or obtained via the peak areas from corresponding HPLC chromatograms.

In some embodiments, the cannabis extract used comprises between 0.01% to 100% w/w cannabinoids, between 1% to 99% w/w cannabinoids, between 1% to 95% w/w cannabinoids, between 1% to 90% w/w cannabinoids, between 1% to 80% w/w cannabinoids, between 1% to 70% w/w cannabinoids, between 1% to 60% w/w cannabinoids, between 1% to 50% w/w cannabinoids, between 1% to 40% w/w cannabinoids, between 1% to 30% w/w cannabinoids. Each possibility is a separate embodiment.

In some embodiments, the tablet comprises between 0.01% to 50% w/w cannabis extract, 0.1% to 20% w/w cannabis extract, 0.1% to 10% w/w cannabis extract, 0.1% to 5% w/w cannabis extract, 1% to 20% w/w cannabis extract, 1% to 10% w/w cannabis extract, 0.1% to 1% w/w cannabis extract. Each possibility is a separate embodiment.

In some embodiments the total amount of THC in the tablet is about 2 mg, about 3 mg, about 5 mg, about 10 mg, about 15 mg, about 20 mg, about 30 mg, about 40 mg, about 50 mg, about 60 mg, about 70 mg, about 80 mg, about 90 mg or about 100 mg. Each possibility is a separate embodiment.

In some embodiments the total amount of CBD in the tablet is about 2 mg, about 3 mg, about 5 mg, about 10 mg, about 15 mg, about 20 mg, about 30 mg, about 40 mg, about 50 mg, about 60 mg, about 70 mg, about 80 mg, about 90 mg or about 100 mg. Each possibility is a separate embodiment.

In some embodiments, the thermogenic agent of the present invention is selected from the list consisting of: Calcium chloride, Sodium sulfate and Magnesium sulfate.

In some embodiments, the thermogenic agent is selected from other metal salts, oxides and/or hydroxides, and suitable such salts are disclosed in U.S. Pat. No. 4,338,098.

In some embodiments, the composition further comprises a polyether, such as, but not limited to: polypropylene glycol (PPG), polyethylene glycol (PEG) and polyethylene-propylene glycol copolymer (PEG/PPG) or any combination thereof. Each possibility is a separate embodiment. In some embodiments, PEG is selected from the list consisting of: PEG 100, 200, 300, 400, 600, 800, 1000, 1100, 1200, 1300, 1400, 1450, 1500, 2000, 2050, 3000, 3350, 3600, 3700, 4000, 4600, 6000, 8000, 10000, 12000, 20000, 35000, 40000, 108000 and 218000.

According to some embodiments, the tablet further comprises one or more of the following: sweetener and flavoring substance.

According to some embodiments, the sweetener is sucralose. According to some embodiments, the final concentration of sucralose may be 0.01% to 0.1%, 0.1% to 1%, 1% to 5%, 0.5% to 2%, 1% to 3%, 0.1% to 5% or 0.1% to 10% by weight. Each possibility is a separate embodiment.

According to some embodiments, the final concentration flavoring substance in the tablet may be 0.01% to 0.1%, 0.1% to 5%, 0.1% to 7%, 1% to 5%, 1% to 7%, by weight. Each possibility is a separate embodiment.

In some embodiments, the flavoring substance is selected from the list consisting of: menthol, vanilla, mango, lemon, strawberry, blueberry, chocolate, blackcurrant, watermelon, pear, anise, pineapple, apple, orange, banana, grapefruit, butter, honey, cherry, melon, mocha, mandarin, apricot, peppermint, grape, caramel, raspberry, cinnamon, kiwi, coffee, cocoa, tea, rum and cola. Each possibility is a separate embodiment.

It is a further object of the present invention to disclose the composition as defined in any of the above, wherein said composition additionally comprises at least one carrier or excipient selected from the group consisting of diluent, solvent, absorbent, anti-adherent, binder, coatings, disintegrant, surfactant, dissolving agent, solubilizing agent, bioadhesive agent, polysaccharides, polymers, copolymers, fast dissolving tablet (FDT) type excipient, bioavailability enhancing agent, Thin Film type excipient, PharmFilm type excipient, mucoadhesive type excipient, acidifying agents, probiotic agents, protective agents, antioxidants, effervescent excipient, dispersing agents, glidant, colours, thickener, lubricant, sorbents, preservatives, and any combination thereof.

In some embodiments, the tablet includes at least 2, 3, 4 or 5 thermogenic agents. Each possibility is a separate embodiment.

EXAMPLES

Example 1—Method for Preparing a Cannabis Extract

Cannabis plant material is ground to a fine powder and cooled to 0° C. Then it is fully covered with cold (0° C.) ethanol for 30 minutes. The mixture is then filtered, separating the liquid from the plant material. The ethanoic liquid containing diluted cannabinoids is then partially evaporated to reach a high concentration of cannabinoids. The concentrated ethanoic extract is winterized to remove waxes by incubation in sub-zero temperature, sedimentation of the waxes and cold filtration of the mixture. The remaining ethanol is then evaporated and an extract in the form of a resin is retained. The extract is then decarboxylated by placing in a 100° C. oven for 4 hours. An extract with 40-90% Cannabinoid content is obtained.

Example 2—Calcium Chloride Tablet Protocol

Sublingual Dry Granulates:
Preparation of Mix1
142.86 g Cannabis extract (66% THC), 14.29 Menthol and 642.86 g Ethanol were added to an empty 2 L stainless-steel container. The container was placed in a water bath at 60° C. and the mixture was homogenized using a magnetic stirrer until fully dissolved.
Preparation of Mix2
728.59 g Mannitol, 57.14 g Kolidon 25, 1648.60 g Avicel PH-101, 8.57 g Sucralose and 142.86 g Croscarmellose sodium were added to an empty Ribbon Powder Mixer and homogenized using the Ribbon Powder Mixer.
Addition of Mix1 into Mix2
2585.7 g of Mix2 and 800.0 g of Mix1 were added to an empty 20 L mixer bowl and homogenized using a 20 L planetary Mixer. The moist mixture was passed through a 0.4-mm sieve, using a granulator apparatus. The moist granulates were then dried in an oven at 60° C. for several hours until a constant weight was obtained, resulting in THC sublingual dry granulates.
Calcium Chloride Pre-Treatment
The calcium chloride powder was dried in a vacuum oven at 250° C. for 10 hours and then passed through a 400-micron sieve, using a granulator apparatus.
Mixing Granulates and Calcium Chloride
480 g of THC sublingual dry granulates, 15 g of croscarmellose sodium and 500 g of dry Calcium chloride were homogenized using a 5 L V-mixer.
5 g of magnesium stearate was then added to the homogenous mixture and homogenized once again using the 5 L V-mixer.
Equivalent Control (Non-Thermogenic) Tablets
Equivalent control (non-thermogenic) tablets can be produced by replacing the 500 g of dry Calcium chloride with 500 g of dry Mannitol, keeping the same ingredients and procedures.
Tableting
Tablet total mass: 300 mg
Dose: 5 mg THC
Tablets were formed using a single punch tablet machine.

Example 3—Thermogenic Tablets Tests

Figure 1:
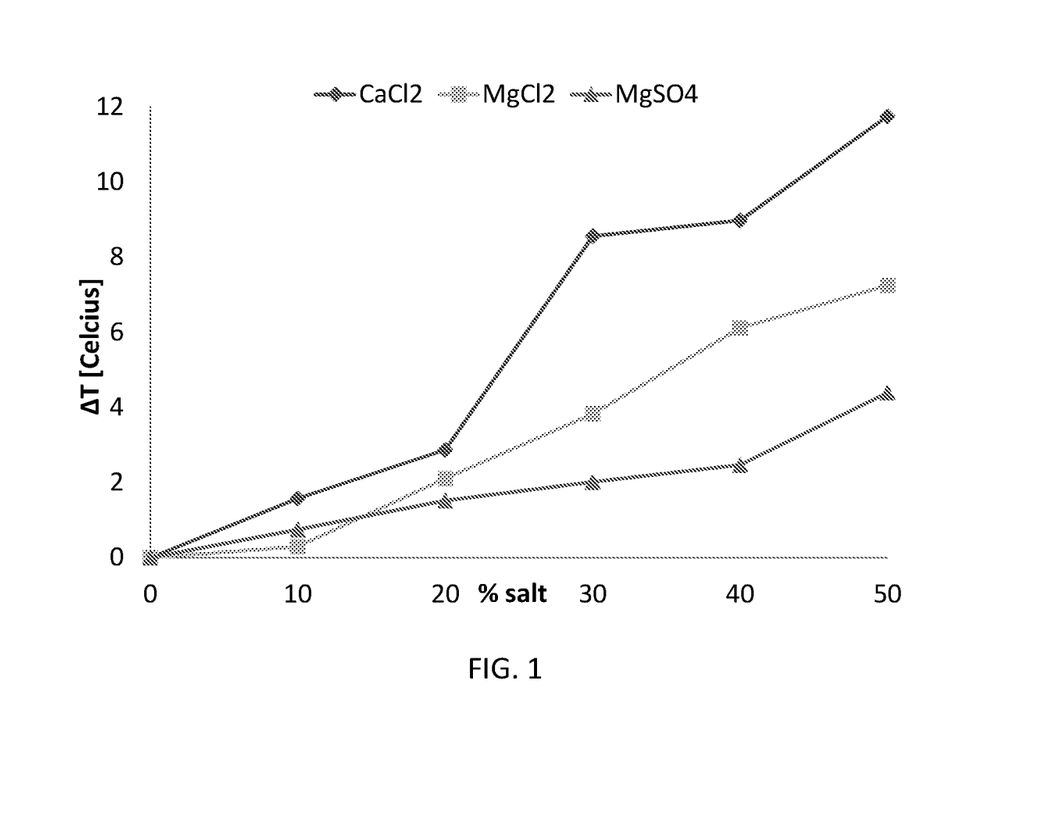
FIG. 1 shows the temperature difference of an aqueous solution before, and after adding tablets comprising cannabis extract, excipients and different quantities of thermogenic salts ($CaCl_2$), $MgCl_2$ or $MgSO_4$).

Sublingual Dry Granulates Preparation
Preparation of Mix1
5 g Cannabis extract (49.5% THC), 0.5 g Menthol and 22.5 g of Ethanol were manually homogenized in a container placed in a hot water bath.
Preparation of Mix2
25.5 g Mannitol, 2 g Kolidon 25, 57.7 g Avicel PH-101, 0.3 g sucralose and 5 g croscarmellose sodium powders were homogenized in a planetary mixer.
Granulation
Mix 2 (90.5 g) and Mix 1 (28 g) were mixed and homogenized in a planetary mixer. The moist mixture was passed through a 400-micron sieve, using a granulator apparatus. The moist granulates were dried in a vacuum oven at 45° C. for several hours until a constant weight was achieved.
Addition of Croscarmellose Sodium
Dry granulates (96 g) and croscarmellose sodium (3 g) were manually homogenized.
Thermogenic Salt Drying
The thermogenic salts (calcium chloride, magnesium chloride, magnesium sulfate) powders were dried in separate containers in a vacuum oven at 180° C. for 4 hours until a constant mass was achieved for each of the salts.
Addition of Dry Thermogenic Salt
To the dry granulates (4.95 g) magnesium stearate (50 mg) and increasing quantities (0 g, 0.56 g, 1.25 g, 2.14 g, 3.33 g, 5 g) of each one of the thermogenic salts (0%, 10%, 20%, 30%, 40%, 50%, respectively, of the total mass) were added followed by homogenization using a vortex apparatus, thereby obtaining 18 mixtures.
Tableting
Tablets (500 mg) were pressed using a Karnavati Minipress II Benchtop Rotary Tablet Press.
Thermogenic Salt Tablets Dissolution Experiment
Experiment Procedure
A water bath was placed on a hot plate using a thermometer set to 37° C. and the water was constantly stirred using a magnetic stirrer to simulate heat regulation within the oral cavity. A 10 ml beaker was placed slightly submerged in the water bath and the temperature within the beaker was monitored using an accurate (0.01° C.) digital thermometer. For each of the 18 samples, ~3 g of tablets were weighed. Water in a ratio of 1:1 (w/w) to tablets was added to the beaker outside of the water bath and was given a few minutes to equalize. Each tablet sample was added to a separate beaker and was manually stirred until temperature reached a maximum. The temperature increase ($\Delta T$) caused by dissolution of the tablet as compared to baseline (just before addition of tablets), was measured using the digital thermometer. FIG. 1 shows the $\Delta T$ of the water/tablets mixture as a function of salt concentration for each of the three salts tested.
As seen from FIG. 1, all tablets elevated the temperature when dissolute in a concentration dependent manner. The most profound increase was obtained for tablets with Calcium chloride (probably due to its higher solubility). It is noted that in-vivo lower salt concentration than those implied by the in-vitro test results may be required.

Example 4—Subjective Efficacy Evaluation of Calcium Chloride Sublingual Cannabis Tablets Subjective efficacy evaluation was performed in order to evaluate the onset of action and the subjective therapeutic efficacy of calcium chloride thermogenic sublingual cannabis tablets compared with non-thermogenic sublingual cannabis tablets. An outline of this experiment, which included 5 volunteers, is presented below.
Both types of tablets contained 168 mg of dry granulates (with 5.4 mg of THC), 5.25 mg croscarmellose sodium and 1.75 mg of magnesium stearate. The thermogenic cannabis tablet contained additional 175 mg CaCl2 (50% out of the total 350 mg of the tablet). The non-thermogenic cannabis tablet contained additional 175 mg mannitol as a filler (50% out of the total 350 mg of the tablet).
Day 1: 3 subjects were given a calcium chloride cannabis tablet and 2 other subjects were given a control, non-thermogenic cannabis tablet, devoid of the calcium chloride. The subjects were not informed of the type of tablet they received.

Day 2: The 2 subjects who the day before were given the control cannabis tablet were given a calcium chloride cannabis tablet and the 3 subjects who the day before took a calcium chloride cannabis tablet were given the control cannabis tablet.

Every 5 minutes during 1 hour, starting immediately before taking the tablet, the subjects reported their subjective evaluation of the cannabis effect on a scale of 0-4, according to the following definitions: 0—without any cannabis effect, 1—slight cannabis effect, 2—moderate cannabis effect, 3—intense cannabis effect, 4—very intense cannabis effect.

Figure 2:
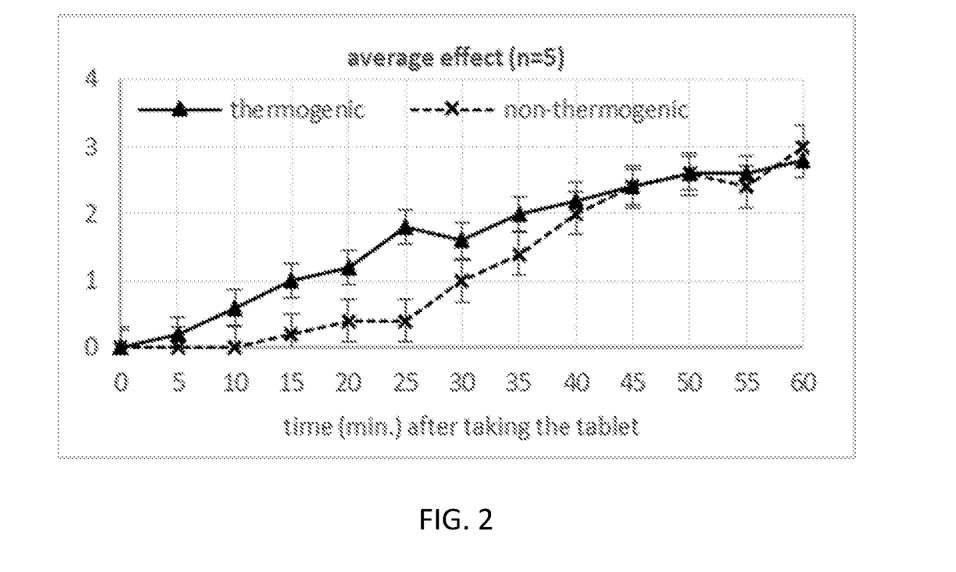
FIG. 2 shows the average effects of thermogenic and non-thermogenic cannabis tablets over time. Error bars represent the standard error.

The average cannabis effects of the thermogenic and non-thermogenic tablets at each time point for all 5 subjects is plotted in FIG. 2. Error bars represent the standard error. The faster onset of the thermogenic tablet, relative to the non-thermogenic tablet, is readily seen. The effect of the thermogenic tablet starts (for some of the subjects) 5-10 minutes after taking the tablet and precedes the effect of the non-thermogenic tablet by 10-15 minutes. The effect of the two tablet types equalize at around 40 minutes after taking the tablet.

Example 5—Clinical Evaluation of the Efficacy of Thermogenic Cannabis Tablets

The clinical efficacy of thermogenic cannabis tablets is further evaluated and demonstrated in a series of clinical studies, as described below.

The sample size of each clinical study is such that it enables demonstrating, in a statistically significant manner, the increased efficacy of the thermogenic cannabis tablets relative to a comparable non-thermogenic cannabis tablet. Both tablet types are similar, apart from the thermogenic agent.

The clinical studies are made blind or double-blind.
A Pharmacokinetics and Objective Efficacy Clinical Study of the Thermogenic Vs. Non-Thermogenic Cannabis Tablets in Healthy Volunteers In this clinical study, healthy volunteers are randomly given the two tablet types for sublingual administration on separate days. Blood samples are taken from the subjects at pre-determined time points starting just before taking the tablets and ending several hours later (e.g. at t=−1, 5, 10, 15, 20, 30, 40, 50, 60, 120, 180, 240 min.). Blood samples are analyzed for the relevant cannabinoids (those that are included in the tablets and their clinically relevant metabolic products, e.g. THC and 11-OH-THC, respectively) to compute and statistically compare pharmacokinetic parameters (e.g. $C_{max}$, $t_{max}$, AUC, bioavailability) between the two tablet types.

The blood sample analysis is also used for comparing the fraction of the tablet's cannabinoid content directly absorbed into the blood stream via the sublingual route and the extent of the first-pass effect between the two tablet types.

During the visit physiological parameters are taken from the volunteers, such as pulse, blood pressure, and/or photograph of the sclera. These parameters are affected by the plasma concentration of some of the cannabinoids (e.g. THC) and hence can be used to statistically compare the physiological effect of the two tablet types.
Clinical Study of the Efficacy of Thermogenic Vs. Non-Thermogenic Cannabis Tablets in Patients In this clinical study, patients are randomly given the two tablet types (test and control) for sublingual administration on separate days. The patients may suffer from conditions for which a fast onset of cannabis effect is beneficial and can be sensed by the patient, e.g. pain.

The patients are given the two types of tablets, which are randomly numbered, and are asked to complete a questionnaire whenever they take a tablet. The questionnaire contains the tablet number and questions regarding the tablet effect (e.g. onset, duration, overall pain reduction) using a self-report pain scale. The questionnaires from all patients are analyzed and the relevant parameters are statistically compared between the two tablet types.

The invention claimed is:

1. A thermogenic cannabis composition for oral administration, the composition comprising at least one cannabinoid and 5/6-60% of at least one anhydrous thermogenic agent, wherein the thermogenic composition is a tablet, a granulate, or a powder suitable for oral administration, and wherein said thermogenic agent comprises an anhydrous metal salt.

2. The thermogenic cannabis composition of claim 1, wherein the thermogenic composition is capable of reaching temperatures of at least 40° C., and no more than 80° C., when exposed to a 37° C. aqueous environment in a 1:1 ratio.

3. The thermogenic cannabis composition of claim 1, comprising 0.1% to 90% w/w of the at least one cannabinoid.

4. The thermogenic cannabis composition of claim 1, comprising 1% to 90% w/w of the at least one cannabinoid.

5. The thermogenic cannabis composition of claim 1, wherein the at least one cannabinoid is selected from the group of Tetrahydrocannabinol (THC), Tetrahydrocannabinolic acid (THCA), Cannabidiol (CBD), Cannabidiolic Acid (CBDA), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Cannabielsoin (CBE), Cannabicitran (CBT) or any combination thereof.

6. The thermogenic cannabis composition of claim 1, comprising 0.1 mg to 100 mg of the at least one cannabinoid per dosage unit.

7. The thermogenic cannabis composition of claim 6, comprising 0.5 mg to 100 mg of the at least one cannabinoid per dosage unit.

8. The thermogenic cannabis composition of claim 7, comprising about 2-25 mg of the at least one cannabinoid per dosage unit.

9. The thermogenic cannabis composition of claim 1, comprising 2/6-70% w/w thermogenic agent.

10. The thermogenic cannabis composition of claim 9, comprising 5/6-60% w/w thermogenic agent.

11. The thermogenic cannabis composition of claim 10, comprising 10%-30% w/w thermogenic agent.

12. The thermogenic cannabis composition of claim 5, comprising about 0.5 mg to about 50 mg CBD or a derivative thereof per dosage unit.

13. The thermogenic cannabis composition of claim 5, comprising about 1 mg to about 20 mg CBD or a derivative thereof per dosage unit.

14. The thermogenic cannabis composition of claim 5, comprising between about 1% w/w to about 10% w/w of CBD or a derivative thereof per dosage unit.

15. The thermogenic cannabis composition of claim 5, comprising about 0.5 mg to about 50 mg THC or a derivative thereof per dosage unit.

16. The thermogenic cannabis composition of claim 5, comprising about 1 mg to about 20 mg THC or a derivative thereof per dosage unit.

17. The thermogenic cannabis composition of claim 1, wherein the metal salt is selected from calcium chloride ($CaCl_2$)), calcium sulfate ($CaSO_4$), calcium nitrate ($Ca(NO_3)_2$), calcium carbonate ($CaCO_3$), calcium oxide (CaOH), calcium bromide ($CaBr_2$), calcium iodide ($CaI_2$), potassium phosphate ($K_3PO_4$), magnesium chloride ($MgCl_2$), magnesium sulfate ($MgSO_4$) magnesium nitrate ($Mg(NO_3)_2$), magnesium carbonate ($MgCO_3$), magnesium bromide ($MgBr_2$), magnesium iodide ($MgI_2$), sodium carbonate ($Na_2NO_3$) potassium carbonate ($K_2NO_3$), sodium acetate ($NaC_2H_3O_2$), potassium acetate ($KC_2H_3O_2$), sodium oxide (NaOH), potassium oxide (KOH), lithium chloride (LiCl), lithium bromide (LiBr), lithium iodide (LiI), lithium sulfate ($Li_2SO_4$) or any combination thereof.

18. The thermogenic cannabis composition of claim 1, further comprising a sweetener and/or a flavoring substance.

19. A method of increasing the efficiency of buccal and/or sublingual absorption of cannabinoids by administering to a subject, in need thereof, the composition of claim 1, thereby increasing the efficiency of buccal and/or sublingual absorption.

\* \* \* \* \*